US006916285B2

(12) United States Patent
Takase

(10) Patent No.: US 6,916,285 B2
(45) Date of Patent: Jul. 12, 2005

(54) ENDOSCOPE DEVICE

(75) Inventor: Seisuke Takase, Hachioji (JP)

(73) Assignee: Olympus Corporation, Tokyo (JP)

( * ) Notice: Subject to any disclaimer, the term of this patent is extended or adjusted under 35 U.S.C. 154(b) by 172 days.

(21) Appl. No.: 10/308,234

(22) Filed: Dec. 2, 2002

(65) Prior Publication Data

US 2003/0158462 A1 Aug. 21, 2003

(30) Foreign Application Priority Data

Dec. 10, 2001 (JP) ........................................ 2001-376251

(51) Int. Cl.[7] .............................................. A61B 1/00
(52) U.S. Cl. ...................................... 600/133; 600/131
(58) Field of Search ................................ 600/102, 131, 600/133, 139

(56) References Cited

U.S. PATENT DOCUMENTS 6,514,198 B2 * 2/2003 Ishibiki ...................... 600/133
6,716,160 B2 * 4/2004 Mitsumori .................. 600/131

FOREIGN PATENT DOCUMENTS

JP           10-286218         10/1998

* cited by examiner

Primary Examiner—Beverly M. Flanagan
(74) Attorney, Agent, or Firm—Straub & Pokotylo; John C. Pokotylo

(57) ABSTRACT

An endoscope device in accordance with the present invention consists mainly of an endoscope, a light source apparatus, a video processor, and a monitor. The endoscope includes an insertion unit, an operation unit, a linkage cord, a connector unit, and an electric connector. The insertion unit is flexible and elongated. The operation unit is coupled to the proximal end of the insertion unit. The endoscope can undergo at least one of cleansing, disinfection, and sterilization that is performed at a high temperature. Furthermore, a drop in the temperature of at least part of the external surface of the operation unit of the endoscope occurring when the endoscope is cooled within a predetermined domain of temperatures is substantially equal to or larger than a drop in the temperature of at least part of the external surface of the insertion unit.

27 Claims, 8 Drawing Sheets

ENDOSCOPE DEVICE

This application claims benefit of Japanese Application No. 2001-376251 filed in Japan on Dec. 10, 2001, the contents of which are incorporated by reference.

BACKGROUND OF THE INVENTION

1. Field of the Invention

The present invention relates to an endoscope device that has an insertion unit which is inserted into, for example, a body cavity, and that can undergo at least one of cleansing, disinfection, and sterilization which is performed at a high temperature.

2. Description of the Related Art

In the past, an endoscope capable of being sterilized with high-pressure steam has been described in Japanese Unexamined Patent Application Publication No. 10-286218 as an example of an endoscope that can be cleansed, or disinfected or sterilized at a high temperature.

The endoscope described in the Japanese Unexamined Patent Application Publication No. 10-286218 has an insertion unit and an operation unit coupled to the insertion unit. The whole endoscope including the insertion unit and operation unit is sterilized with high-pressure steam.

However, as far as the endoscope described in the Japanese Unexamined Patent Application Publication No. 10-286218 is concerned, when the temperature thereof becomes equal to or higher than 130° C. through high-pressure steam sterilization, the endoscope cannot be used until the temperature of the insertion unit that is inserted into a body cavity decreases to be low enough. However, even when the temperature of the insertion unit is low, the temperature of the operation unit which an operator holds during use may be still high. If the operator's hand sweats during examination, the operator may feel uncomfortable or may be annoyed with poor maneuverability.

OBJECT AND SUMMARY OF THE INVENTION

An object of the present invention is to provide an endoscope device in which after high-pressure steam sterilization is completed, when the temperature of an insertion unit decreases to a value permitting examination, the temperature of an operation unit is equal to or lower than the temperature of the insertion unit without fail. During examination, an operator will not feel uncomfortable but enjoy excellent maneuverability.

Briefly, according to the present invention, an endoscope device has an insertion unit and an operation unit coupled to the insertion unit, and can undergo at least one of cleansing, disinfection, and sterilization that is performed at a high temperature. A drop in the temperature of at least part of the external surface of the operation unit occurring when the operation unit is cooled within a predetermined domain of temperatures is substantially equal to or larger than a drop in the temperature of at least part of the external surface of the insertion unit. Owing to this structure, the drop in the temperature of at least part of the external surface of the operation unit occurring when the operation unit is cooled within the predetermined domain of temperatures is substantially equal to or larger than the drop in the temperature of at least part of the external surface of the insertion unit. Consequently, after high-pressure steam sterilization is completed, when the temperature of the insertion unit decreases to a value permitting examination, the temperature of the operation unit is equal to or lower than the temperature of the insertion unit without fail. During examination, an operator will not feel uncomfortable but enjoy excellent maneuverability.

The above object of the present invention and the advantage thereof will be further apparent from the detailed explanation below.

DETAILED DESCRIPTION OF THE PREFERRED EMBODIMENTS

Figure 1:
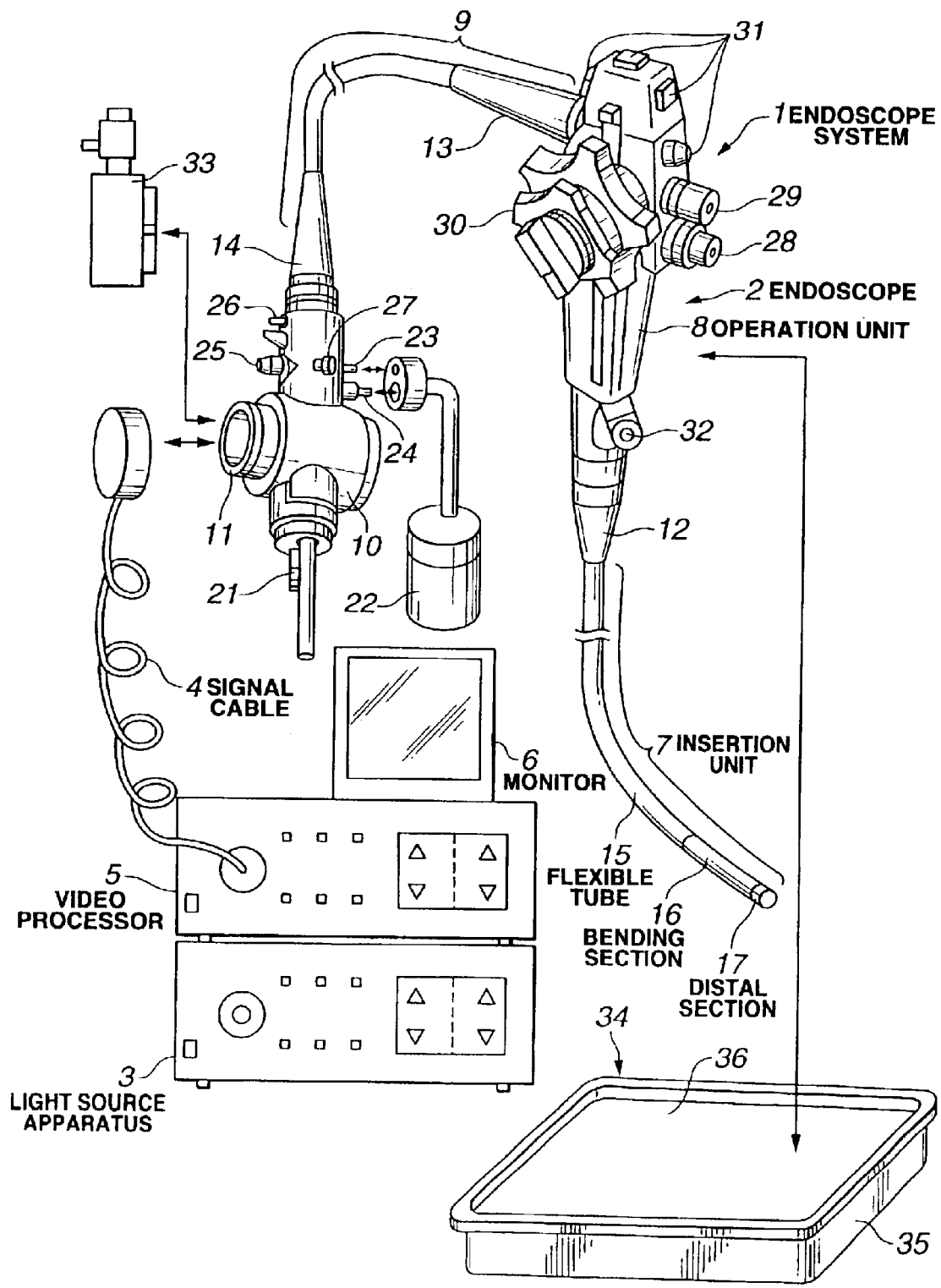
FIG. 1 is an explanatory diagram showing the overall configuration of an endoscope device in accordance with a first embodiment of the present invention.

Referring to the drawings, embodiments of the present invention will be described below.

(First Embodiment)

Figure 2:
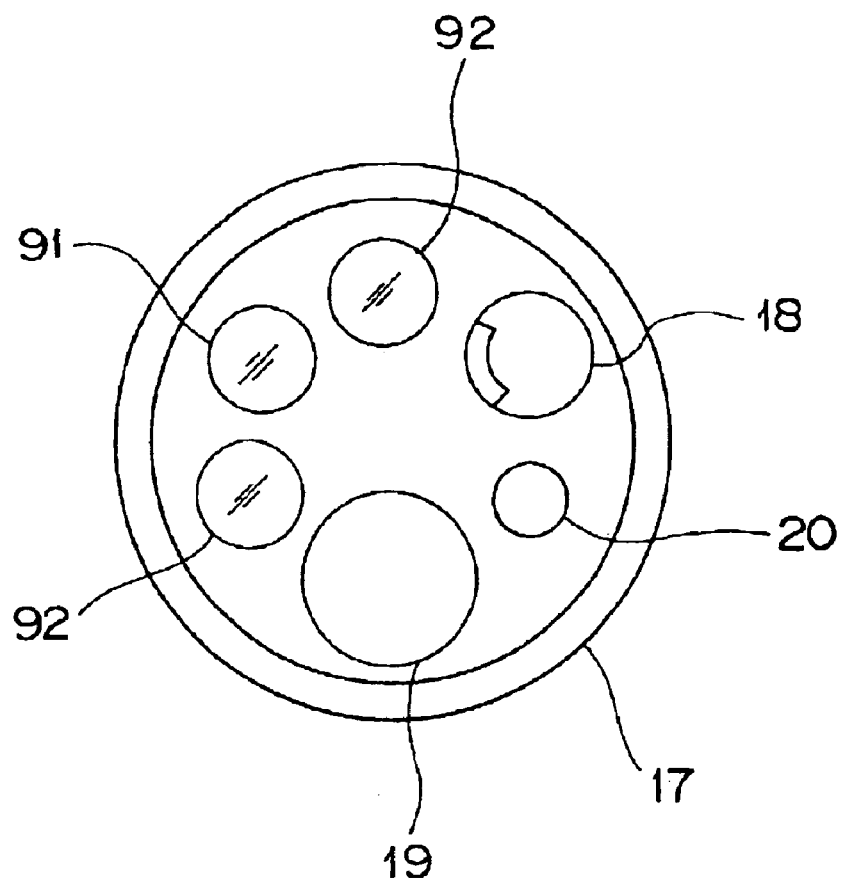
FIG. 2 is a front view of a distal section of an insertion unit included in the endoscope device in accordance with the first embodiment of the present invention.
Figure 3:
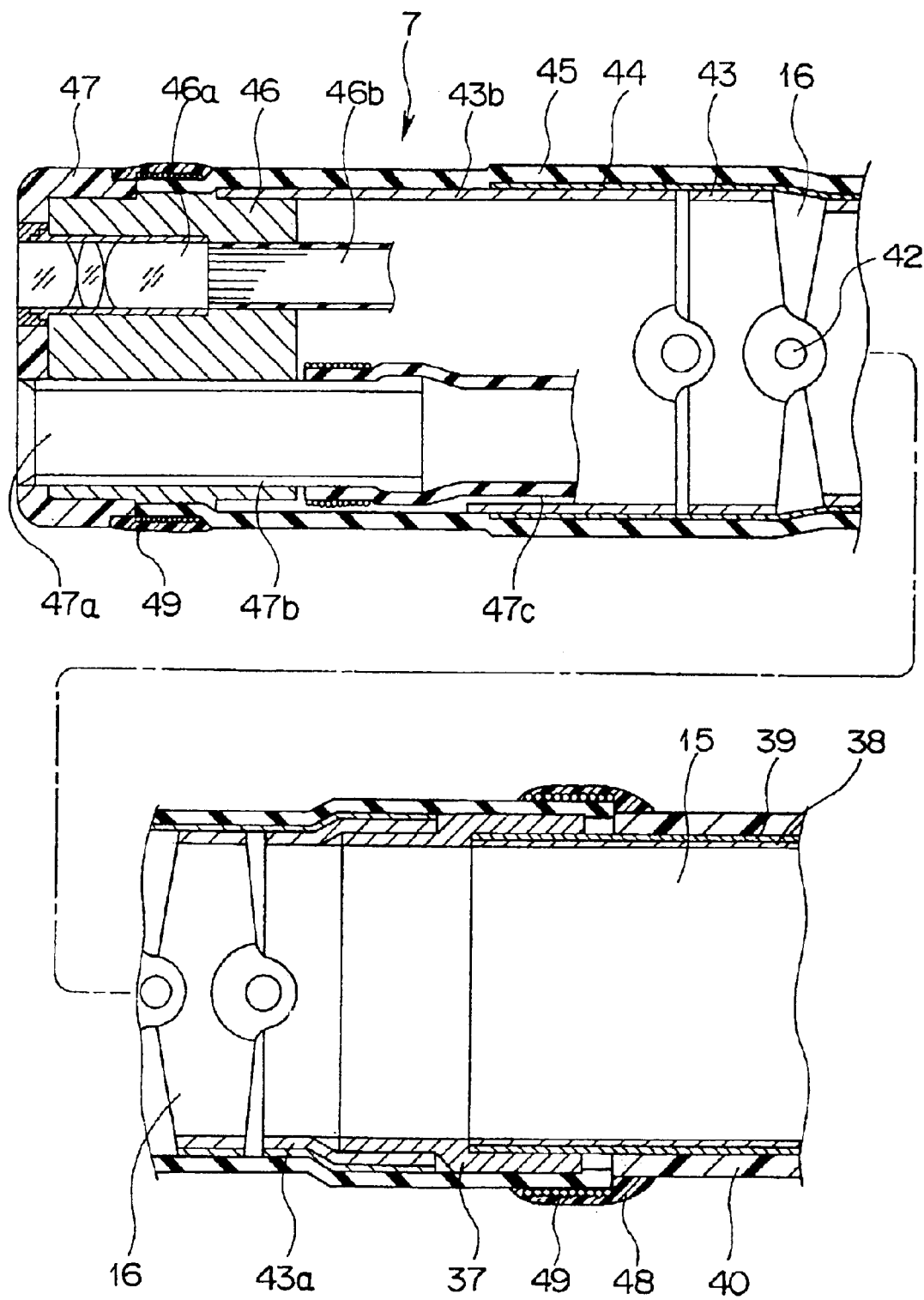
FIG. 3 is a sectional view of the distal and proximal portions of the insertion unit of the endoscope device in accordance with the first embodiment of the present invention.
Figure 4:
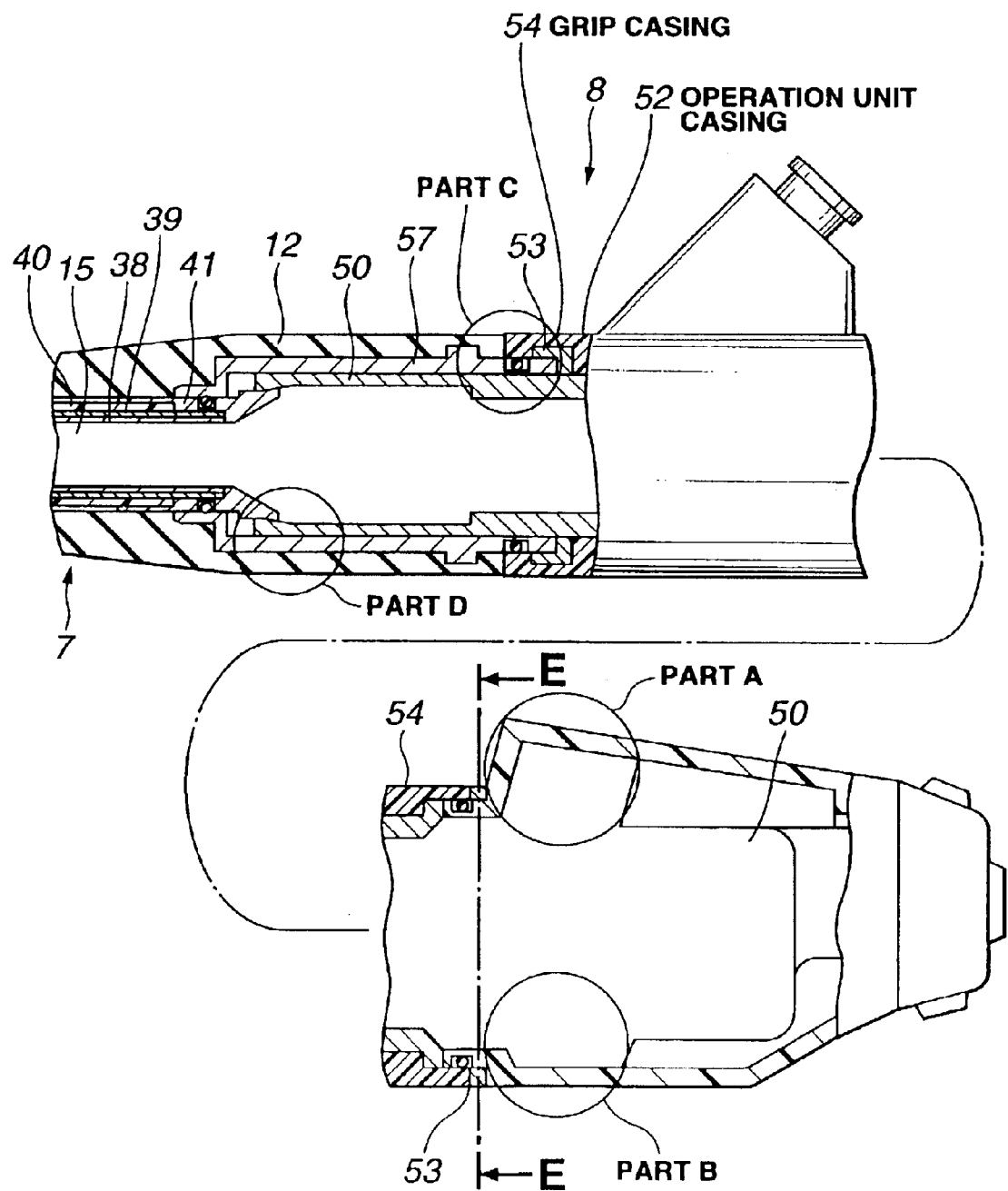
FIG. 4 is a sectional view of an operation unit included in the endoscope device in accordance with the first embodiment of the present invention.
Figure 5:
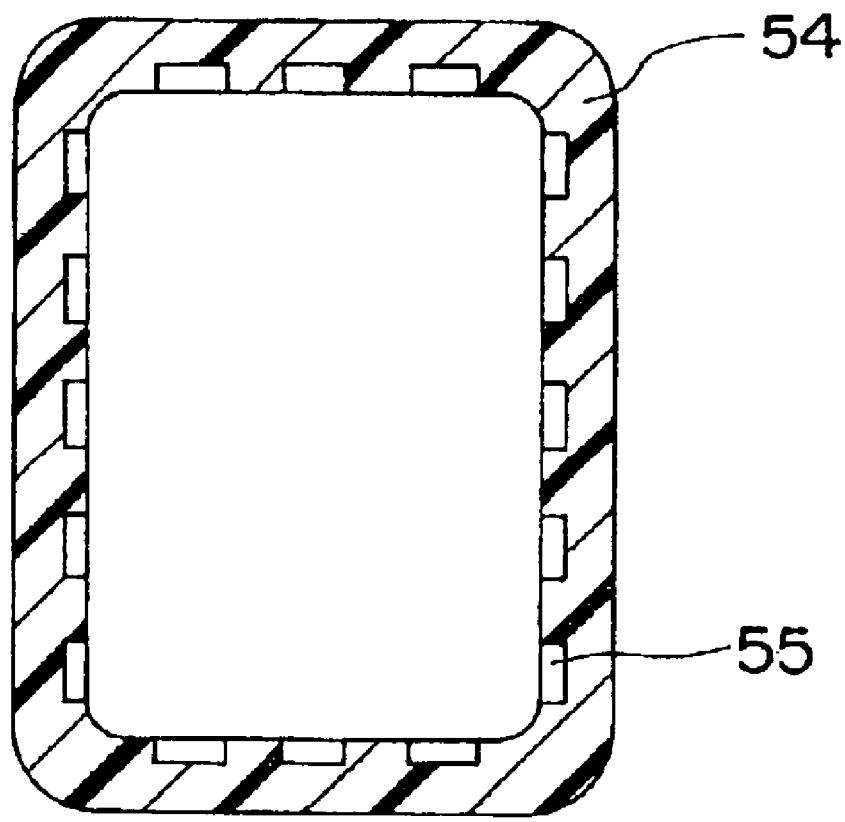
FIG. 5 is an E—E sectional view of the operation unit included in the first embodiment of the present invention which is shown in FIG. 4.

FIG. 1 to FIG. 5 are concerned with a first embodiment of the present invention. FIG. 1 is an explanatory diagram showing the overall configuration of an endoscope device. FIG. 2 is a front view of a distal section of an insertion unit included in the endoscope device. FIG. 3 is a sectional view showing the distal and proximal portions of the insertion unit included in the endoscope device. FIG. 4 is a sectional view of an operation unit included in the endoscope device. FIG. 5 is an E—E sectional view of the operation unit shown in FIG. 4.

(Configuration)

FIG. 1 shows the overall configuration of the endoscope device.

As shown in FIG. 1, the endoscope device 1 consists mainly of an endoscope 2, a light source apparatus 3, a video processor 5, and a monitor 6.

The endoscope 2 has an image pickup means that will be described later. The light source apparatus 3 is connected to the endoscope 2 such that it can be disconnected freely, whereby illumination light is supplied to a light guide lying through the endoscope 2. The video processor 5 that is connected to the endoscope 2 over a signal cable 4 controls the image pickup means incorporated in the endoscope 2, and processes a signal produced by the image pickup means. An image corresponding to a subject image and being represented by a video signal transferred from the video processor 5 is displayed on the monitor 6.

The endoscope 2 has an insertion unit 7, an operation unit 8, a linkage cord 9, a connector unit 10, and an electric connector 11.

The insertion unit 7 is flexible and elongated. The operation unit 8 is connected to the proximal end of the insertion unit 7. The linkage cord 9 is flexible and extending from the lateral side of the operation unit 8. The connector unit 10 is coupled to the end of the linkage cord 9, and connected to the light source apparatus 3 such that it can be disconnected freely. The electric connector 11 is located on the lateral side of the connector unit 10. The signal cable 4 plugged into the video processor 5 can be coupled to the electric connector 11 such that it can be uncoupled freely.

The electric connector 11 has a vent which is not shown and through which the interior and exterior of the endoscope 2 communicate with each other.

The joint of the insertion unit 7 and operation unit 8 has an insertion unit anti-breakage member 12 that includes an elastic member and that prevents the joint from being bent too sharply. The joint of the operation unit 8 and linkage cord 9 has an operation unit anti-breakage member 13 analogous to the insertion unit anti-breakage member 12. Furthermore, the joint of the linkage cord 9 and connector unit 10 has a connector unit anti-breakage member 14 analogous to the insertion unit anti-breakage member 12.

The insertion unit 7 has a flexible tube 15, a bending section 16, and a distal section 17 concatenated with one another in the order mentioned from the proximal end of the insertion unit 7.

The flexible tube 15 is flexible and soft. The bending section 16 is provided at the distal end of the flexible tube 15 and bendable by handling the operation unit 8. The distal section 17 has an observation optical system and an illumination optical system, which will be described later, disposed at the distal end thereof.

As shown in FIG. 2, the distal section 17 has an aeration/perfusion nozzle 18 serving as an air and water outlet, a suction port 19, a fluid supply port 20, an observation optical system 91, and an illumination optical system 92.

The aeration/perfusion nozzle 18 jets out a cleanser or a gas to an optical member that serves as an external surface of the observation optical system 91. The suction port 19 is a distal opening of a therapeutic instrument channel through which a therapeutic instrument lying through the insertion unit 7 is thrust forward or an intracavitary fluid is sucked. The fluid supply port 20 opens onto an object of observation and serves as an opening through which a fluid is jetted out to the object of observation.

As shown in FIG. 1, the connector unit 10 includes a gas supply base 21, a water tank pressurization base 23, a fluid supply base 24, a suction base 25, an injection base 26, and a ground base 27.

The gas supply base 21 is connected to a gas supply source that is not shown and that is incorporated in the light source apparatus 3 such that it can be freely disconnected. The water tank pressurization base 23 and fluid supply base 24 are connected to a water tank 22 that is a fluid supply source. The suction base 25 is connected to a suction source that is not shown and that is used to suck a fluid through the suction port 19 shown in FIG. 2. The injection base 26 is connected to a water supplying means that is not shown and that supplies water through the fluid supply port 20 shown in FIG. 2. If a high-frequency leakage current flows through the endoscope 2 because of diathermic treatment or the like, the leakage current is fed back to a diathermic therapeutic instrument through the ground base 27.

The operation unit 8 has an aeration/perfusion button 28, a suction button 29, an angling knob 30, a plurality of remote switches 31, and a therapeutic instrument insertion port 32.

The aeration/perfusion button 28 is an operating member for aeration or perfusion. An operator presses the aeration/perfusion button 28, whereby an organ is aerated or perfused through the aeration/perfusion nozzle 18 shown in FIG. 2. The suction button 29 is an operating member to be used for a suction, whereas the operator can perform a suction through the suction part 19, shown in FIG. 2, by pressing the suction button 29. The angling knob 30 is an operating member to be used to bend the bending section 16. The plurality of remote switches 31 are operating members to be used to remotely control the video processor 5. The therapeutic instrument insertion port 32 is a proximal opening that communicates with the therapeutic instrument channel.

A waterproof cap 33 that seals the inside of the electric connector 11 of the endoscope 2 so as to keep it watertight can be freely detachably attached to the electric connector 11. The waterproof cap 33 has a pressure adjustment valve that is not shown.

For high-pressure steam sterilization, a sterilization storage case 34 is used to store the endoscope 2.

The storage case 34 is composed of a tray 35 and a lid member 36.

The tray 35 and lid member 36 have a plurality of vents that are not shown. Steam permeates through the vents.

The tray 35 has a restricting portion that is not shown and that is outlined similarly to the endoscope 2. The restricting portion of the tray 35 is shaped such that the components of the endoscope 2 will be fitted in predetermined places.

Furthermore, the restricting portion of the tray 35 includes an insertion unit restricting portion that is not shown. The flexible and elongated insertion unit 7 is stored in the insertion unit restricting portion.

The ANSI/AAMI ST37-1992 approved by the American National Standards Institute and issued by the Association for the Advancement of Medical Instrumentation stipulates as typical conditions for high-pressure steam sterilization that a pre-vacuum type sterilization step should be performed at 132° C. for four minutes and a gravity-type sterilization step should be performed at 132° C. for ten minutes.

The condition of a temperature for a sterilization step within high-pressure steam sterilization varies depending on the model of high-pressure steam sterilization apparatus or the duration of the sterilization step. In general, the temperature ranges from about 115° C. to about 138° C. Some sterilization apparatuses can be set to about 142° C.

The condition of a duration varies depending on the temperature condition for a sterilization step. In general, the duration ranges from about 3 minutes to about 60 minutes. Some sterilization apparatuses may be set to about 100 minutes.

The pressure in a sterilization chamber at the sterilization step is set to a pressure higher than an atmospheric pressure by about 0.2 Mpa.

A typical pre-vacuum type high-pressure steam sterilization method consists of a pre-vacuum step at which a sterilization chamber in which equipment to be sterilized is placed is depressurized prior to a sterilization step and a sterilization step which succeeds the pre-vacuum step and at which high-pressure high-temperature steam is fed into the sterilization chamber for sterilization. The pre-vacuum step is a step at which steam is permeated through the details of the equipment to be sterilized. That is, when the sterilization chamber is depressurized, high-pressure high-temperature steam permeates through the equipment to be sterilized.

The pressure in the sterilization chamber at the pre-vacuum step is generally set to a pressure lower than the atmospheric pressure by a pressure ranging from about −0.07 MPa to about −0.09 MPa.

An example of high-pressure steam sterilization may include a dry step, at which the sterilization chamber is depressurized again, as a step succeeding the sterilization step so that the sterilized target equipment can be dried up after the sterilization step. At the dry step, the sterilization chamber is depressurized in order to exhaust steam from the sterilization chamber and to thus facilitate drying of the equipment to be sterilized in the sterilization chamber. The pressure in the sterilization chamber at the dry step is generally set to a pressure lower than the atmospheric pressure by a pressure ranging from about −0.07 MPa to about −0.09 MPa.

Sterilization of the endoscope 2 with high-pressure steam is performed in a state that the waterproof cap 33 with a pressure adjustment valve attached to the electric connector 11. In this state, the pressure adjustment valve of the waterproof cap 33 which is not shown is closed. The vent of the electric connector is blocked with the waterproof cap 33, whereby the interior of the endoscope is sealed from the exterior and kept watertight.

In a sterilization method including a pre-vacuum step, the pressure in the sterilization chamber is decreased at the pre-vacuum step so that the external pressure of the endoscope 2 will be lower than the internal pressure thereof. The difference in pressure causes the pressure adjustment valve to open. Consequently, the interior of the endoscope 2 communicates with the exterior thereof via the vent. This prevents a large difference from occurring between the internal pressure of the endoscope 2 and the pressure in the sterilization chamber. Consequently, the endoscope 2 will not be broken because of the pressure difference between the interior thereof and the exterior thereof.

At the sterilization step, the sterilization chamber is pressurized so that the external pressure of the endoscope 2 will get higher than the internal pressure thereof. This pressure difference causes the pressure adjustment value to close. Consequently, the high-pressure high-temperature steam does not actively invade via the waterproof cap 33 and vent into the interior of the endoscope 2.

However, the high-pressure high-temperature steam invades little by little through O rings or the like that are made of a fluoro-rubber or a silicon rubber and that are seal means included in junctions of an armor of the flexible tube 15, made from macromolecule, and in junctions of a housing of the endoscope 2.

The housing of the endoscope 2 withstands a pressure that is oriented from outside to inside and that is calculated as a sum of a pressure by which the sterilization chamber is depressurized at the pre-vacuum step and a pressure by which the sterilization chamber is pressurized at the sterilization step.

According to a method including a depressurization step as a step succeeding a sterilization step, the pressure in the sterilization chamber is decreased at the depressurization step so that the external pressure of the endoscope 2 will get lower than the internal pressure thereof. When the pressure difference occurs, the pressure adjustment valve opens nearly at the same time. Consequently, the interior of the endoscope 2 communicates with the exterior thereof via the vent. This prevents occurrence of a large pressure difference between the interior of the endoscope 2 and the sterilization chamber. Therefore, a breakage of the endoscope 2 by a pressure difference between the interior thereof and the exterior thereof will not happen.

After the depressurization step is completed, the sterilization chamber is pressurized so that the external pressure of the endoscope 2 will get higher than the internal pressure thereof. When the pressure difference occurs, the pressure adjustment valve closes.

When all the steps for high-pressure steam sterilization are completed, a pressure oriented from outside to inside exists on the housing of the endoscope 2. The pressure amount corresponds to an amount by which the sterilization chamber is depressurized.

When the waterproof cap 33 is detached from the electric connector 12, the interior of the endoscope 2 communicates with the exterior thereof via the vent. The internal pressure of the endoscope 2 becomes equal to the atmospheric pressure. The endoscope 2 is relieved from a load of a pressure imposed on the housing of the endoscope 2.

Next, a major portion of the first embodiment will be described in conjunction with FIG. 3 to FIG. 5.

FIG. 3 shows the structure of the distal portion of the insertion unit 7.

As shown in FIG. 3, the proximal end of the bending section 16 is fixed to a distal metal fitting 37 that is a metallic member made of a stainless steel or the like and that is included in the flexible tube 15.

The proximal portion of the flexible tube 15 is composed of a helical tube 38, a braid tube 39 woven using a stainless steel thread in the form of a net and used to sheath the periphery of the helical tube 38, and an armor layer 40 made of a resin and used to sheath the external surface of the helical tube 38 in close contact therewith.

The armor layer 40 is made of an amide elastomer, a styrene resin, a fluorocarbon resin, or a silicon rubber.

The bending section 16 has as a basic structure a plurality of joint members 43 that are made of a metal such as a stainless steel. The joint members 43 are shaped like short cylinders, and concatenated with rivets 42 so that they can pivot freely. The bending section 16 also has a braid tube 44 which is woven using a metallic thread and which covers the external surfaces of the joint members 43. The external surface of the braid tube 44 is sheathed with an armor tube 45 that is flexible and made of a resin such as a fluoro rubber.

A proximal joint member 43a among the joint members 43 is engaged with the distal metal fitting 37 of the flexible tube 15 and fixed thereto using a screw or the like.

A distal joint member 43b among the joint members 43 is fixed to a distal body 46, which is made of a metal such as a stainless steel, using a screw or the like. The distal body 46 has an observation optical system 91 shown in FIG. 2 or any other objective optical system incorporated therein.

An isolating cover member 47, made of a resin that is highly chemical-resistant and is also heat-resistant to resist a temperature higher than the temperature of high-pressure steam used in a high-pressure steam sterilization method, such as, polyphenylsulfone, polysulfone, polyether sulfone, or polyether ether ketone, is engaged with the external surface of the distal body 46.

The proximal portion of the armor tube 45 sheathes the distal portion of the flexible tube 15, and the proximal end thereof abuts on the armor layer 40. At both ends of the armor tube 45, the armor tube 45 has the external surface thereof bound with a fixing thread 49, and is pressed against the internal distal body 46 and distal metal fitting 37 respectively, and is thus immobilized.

An adhesive 48 made of an epoxy resin or the like is applied over the external surface of the fixing thread 49 wound about the distal end of the armor tube 45 in such a manner that it covers the armor tube 45, fixing thread 49, and isolating cover member 47. The adhesive 48 applied to the distal end of the armor tube covers the fixing thread 49 and seals the border between the isolating cover member 47 and armor tube 45 so as to keep it watertight.

The adhesive 48 is applied to the external surface of the fixing thread 49 wound about the proximal end of the armor tube 45 in such a manner that it covers the armor tube 45, fixing thread 49, and armor layer 40. The adhesive applied to the proximal end of the armor tube covers the fixing thread 49 and seals the border between the armor layer 40 and armor tube 45 so as to keep the border watertight.

Next, the proximal portion of the insertion unit 7 (flexible tube 15) and the operation unit 8 will be described in conjunction with FIG. 4.

The proximal portion of the insertion unit 7 (flexible tube 15) has a joint metal fitting 41, which is a metallic member made of a stainless steel or the like, engaged with the helical tube 38 and braid tube 39 that are located inside the joint metal fitting 41.

The external surface of the braid tube 39 is in close contact with the internal surface of the joint metal fitting 41, and the ends of the helical tube 38 and braid tube 39 abut on the joint metal fitting 41 in close contact therewith.

The operation unit 8 has a chassis 50 that is a metallic member made of aluminum or the like and exhibiting excellent heat conductivity. The chassis 50 has an angling mechanism or the like that is not shown and that is used to bend the bending section 16.

The chassis 50 may be formed with a single metallic member or made by concatenating a plurality of metallic members.

The distal portion of the chassis 50 is engaged with the joint metal fitting 41 included in the proximal portion of the flexible tube 15.

The proximal portion of the chassis 50 is coupled to a joint metal fitting that is not shown. The joint metal fitting is a metallic member made of a stainless steel or aluminum and used to join the chassis with the linkage cord 9.

Incidentally, the linkage cord 9 has the same structure as the flexible tube 15.

An operation unit casing 52 is mounted on the external surface of the chassis 50 so that the interior of the chassis 50 and the angling mechanism and others which are not shown can be kept watertight.

The operation unit casing 52 is composed of a plurality of members and includes a grip casing 54 by which an operator grasps the operation unit so as to handle the operation unit.

The grip casing 54 is made of a resin that withstands high-pressure steam sterilization, such as, polyphenylsulfone, polysulfone, polyether sulfone, polyether ether ketone, polyphenylsulfide, polyether imide, or a liquid crystal polymer.

The grip casing 54 is designed so that it will meet the chassis 50 and the angling mechanism that is not shown, for example, part A and part B shown in FIG. 4.

Moreover, a heat absorbing member 53 made of a resin material, an elastomer material, or a metallic material, which offers a heat conductivity higher than the material made into the grip casing 54, may be interposed between the grip casing 54 and an adjoining member. Consequently, the heat absorbing member 53 absorbs heat dissipated from the grip casing 54. Moreover, for example, heat may be conveyed to the chassis so or an insert fitting 57, which is made of a metallic material, by way of the heat absorbing member 53 included in part C shown in FIG. 4. This, facilitates cooling of the grip casing 54.

In terms of combinations of a selection of materials to be made into the members constituting the bending section 16 and operation unit 8, a setting of a method of joining members and the areas of the portions of members that meet each other, a setting of the areas of the portions of the chassis 50 and grip casing 54 that meet each other, and the number of heat absorbing members 53 interposed between the grip casing 54 and chassis 50, the insertion unit 7 and operation unit 8 are designed as described below.

Assuming that the foregoing members having substantially the same temperatures are cooled in a temperature environment ranging from, for example, about 35° C. to about 140° C., according to the first embodiment, a drop in the temperature of the external surface of the insertion unit 7, that is, the temperatures of the external surfaces of the isolating cover member 47, armor tube 45, armor layer 40, and adhesive 48 occurring for a certain time interval is set smaller than a drop in the temperature of the external surface of the grip casing 54.

The upper limit of the range of temperatures, that is, 140° C. is the highest temperature the endoscope 2 undergoes when heated according to the high-pressure steam sterilization method. The lower limit thereof, that is, 35° C. is substantially the same as the body temperature. When the insertion unit 7 of the endoscope 2 is inserted into a body cavity of a subject, if the temperature of the insertion unit 7 is 35° C., the subject will not complain about the temperature.

According to the first embodiment, concrete components described below are employed in order to satisfy the aforesaid conditions.

As a material to be made into the grip casing 54, a material whose heat conductivity is better than that of the resin materials made into the isolating cover member 47, armor tube 45, armor layer 40, and adhesive 48 respectively is selected. For example, the isolating cover member 47 is made of polyether sulfone, the armor tube 45 is made of a fluoro rubber, the armor layer 40 is made of an amide elastomer, and the adhesive 48 is made of an epoxy resin. In this case, a resin exhibiting better heat conductivity than that of these materials is adopted for the grip casing 54. The grip casing 54 is disposed to meet the chassis 50 that is a metallic member.

Moreover, the anti-breakage member 12 made of a rubber material and having the insert fitting 57, which is made of a metallic material, attached to the internal surface thereof is provided in the distal portion, that adjoins the insertion unit of the operation unit casing 52.

The insert fitting 57 is, as shown in part C in FIG. 4, positioned to abut on the grip casing 54 and to meet the chassis 50.

On the other hand, the joint metal fitting 41 coupled to the insertion unit 7 and the chassis 50 are, as shown in part D in FIG. 4, positioned not to meet each other.

Incidentally, the base resin material of the grip casing 54 may not exhibit the best heat conductivity. For example, the resin material may be blended with a glass filler or any other resin so that the blend will exhibit the best heat conductivity.

As shown in FIG. 5, a plurality of notches 55 may be formed in the grip casing 54 in order to increase the area of a heat radiating portion of the grip casing 54. In this case, the grip casing 54 will be cooled efficiently.

Owing to the foregoing structures, the endoscope device 1 having the insertion unit 7 and the operation unit 8 coupled to the insertion unit 7 can undergo at least one of cleansing, disinfection, and sterilization that is performed at a high temperature.

Furthermore, in the endoscope device 1, a drop in the temperature of at least part of the external surface of the operation unit 8 occurring when the operation unit is cooled within a predetermined domain of temperatures is substantially equal to or larger than a drop in the temperature of at least part of the external surface of the insertion unit 7.

(Action)

The endoscope 2 is heated up to approximately 140° C. at a sterilization step of a high-pressure steam sterilization method. When the endoscope 2 is taken out of a sterilization apparatus, the temperature of the endoscope 2 generally ranges from substantially 80° C. to 130° C.

Before the endoscope 2 is used for examination, the endoscope 2 is left intact or forcibly cooled using cold water or air.

The grip casing 54 meets the chassis 50 that is a metallic member exhibiting excellent heat conductivity. Moreover, the grip casing 54 abuts on the insert fitting 57 that is engaged with the internal surface of the insertion unit anti-breakage member 12 and that is a metallic member exhibiting excellent heat conductivity. When the heat absorbing member 53 is included, the grip casing 54 abuts on the heat absorbing member 53.

When the endoscope 2 is taken out of the sterilization apparatus, the chassis 50 and insert fitting 57 that are metallic members exhibiting excellent heat conductivity and meet the grip casing 54 which is an outline member are cooled.

If the area of the portions of the grip casing 54 and chassis 50 that meet each other is large enough, cooling is facilitated.

Consequently, heat dissipated from the grip casing 54 made of a material exhibiting excellent heat conductivity is conveyed to the metallic members that are the chassis 50 and insert fitting 57, the heat absorbing member 53 that is a heat absorbing member, and the helical tube 38 and braid tube 39 to which the insert fitting 57 is connected via the chassis 50 and joint metal fitting 41. Thus, cooling of the grip casing 54 is facilitated.

Moreover, the material made into the grip casing 54 exhibits better heat conductivity than that of the material made into the isolating cover member 47, armor tube 45, and armor layer 40. The grip casing 54 is cooled more efficiently than these members are.

Heat dissipated from the isolating cover member 47, armor tube 45, and armor layer 40 which constitute the external surface of the insertion unit 7 and which exhibit poorer heat conductivity than that of the grip casing 54 is conveyed to the metallic members in contact with them. Cooling is thus facilitated.

Consequently, when a certain time interval has elapsed since start of cooling, the temperature of the grip casing 54 is equal to or lower than the temperature of any part of the external surface of the insertion unit 7.

Consequently, when the insertion unit 7 is cooled to have a temperature permitting insertion of the insertion unit 7 into a body cavity, the temperature of the grip casing 54 is equal to or lower than that of the insertion unit 7 without fail.

Incidentally, the heat absorbing member 53 may not be formed. Instead, the area of the portions of the grip casing and insert fitting 57 that meet each other may be made large enough. Thus, thermal conduction may be facilitated.

(Advantages)

According to the first embodiment, the temperature of the insertion unit 7 permitting insertion of the insertion unit into a body cavity is about 35° C. At this time, the temperature of the grip casing 54 is equal to or lower than that of the insertion unit 7 without fail. When an operator uses the endoscope device, the operator will not find the temperature of the grip casing 54 too high to hold the grip casing, or will not feel uncomfortable even if his/her hand, with which the grip portion is held, sweats. Thus, excellent maneuverability will be maintained.

(Second Embodiment)

Figure 6:
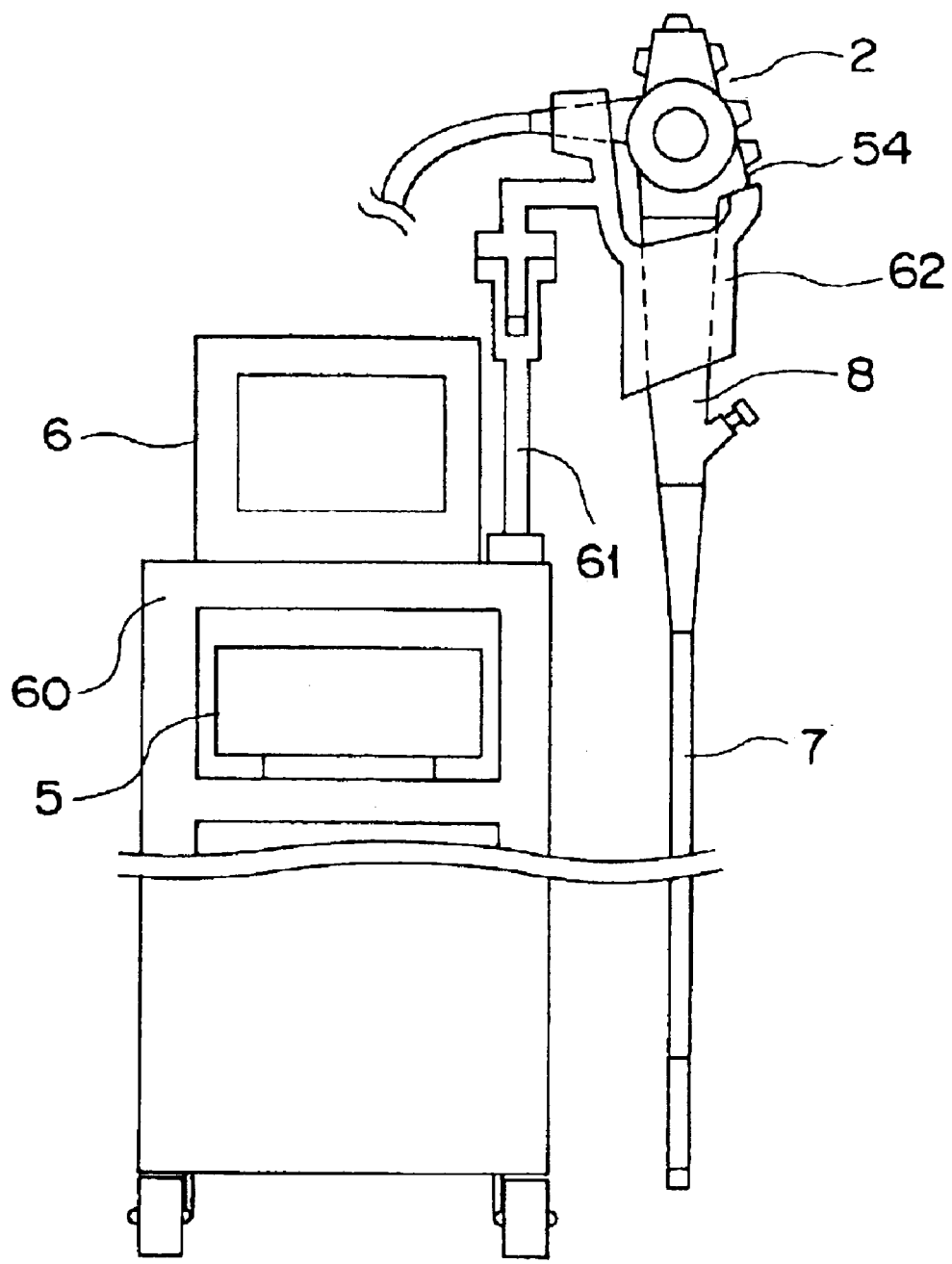
FIG. 6 is an explanatory diagram concerning a case where the components of an endoscope device in accordance with a second embodiment of the present invention are integrated into a cart.

FIG. 6 is an explanatory diagram concerning a case where the components of an endoscope device in accordance with a second embodiment of the present invention are integrated into a cart.

(Configuration)

FIG. 6 shows the placement of the endoscope 2 attained before an operator uses the endoscope 2.

As shown in FIG. 6, the endoscope 2 and peripheral equipment including the light source apparatus 3, video processor 5, and monitor 6 which are shown in FIG. 1 are integrated into a cart 60.

Moreover, the cart 60 has a holder member 62 in which the endoscope 2 is placed and a support member 61 that is made of a metallic material and that bears the holder member 62.

When the endoscope 2 is placed on the cart 60, the grip casing 54 of the endoscope 2 is abutted against the holder member 62.

The abutment surface of the holder member 62 against which the grip casing 54 is abutted has a portion thereof brought into contact with the grip casing 54. When the area of the portion is made large enough, heat dissipated from the grip casing 54 is efficiently conveyed to the holder member 62. Moreover, the holder member 62 is made of a material exhibiting excellent heat conductivity.

(Action)

Normally, before examination is started, the endoscope 2 is placed in the holder member 62 of the cart 60 as shown in FIG. 6. At this time, heat dissipated from the grip casing 54 is readily conveyed to the support member 61 via the holder member 62. Consequently, the grip casing 54 is cooled efficiently.

(Advantages)

The second embodiment has the same advantages as the first embodiment does. In addition, the second embodiment can further facilitate cooling of the grip casing 54.

According to the present invention, a setting of a heat conductivity to be offered by each material or presence or absence of a heat insulating member need not follow the present embodiment. Various features may be combined so that a drop in the temperature of the external surface of one member of the endoscope occurring for a certain time interval will have a desired relationship with a drop in the temperature of the external surface of another member.

(Third Embodiment)

Japanese Unexamined Patent Application Publication No. 2-283346 describes an endoscope having an insertion unit that includes a flexible tube which has an armor layer made of a resin as an external surface thereof.

When the endoscope described in the Japanese Unexamined Patent Application Publication No. 2-283346 is sterilized with high-pressure steam, the armor resin of the flexible tube of the insertion unit is denatured. There is a possibility that the insertion unit may lose required properties.

An object of the third embodiment described below is to provide an endoscope capable of ensuring excellent inserting smoothness. Specifically, the denaturation of a resin made into a flexible tube occurring when the endoscope is sterilized with high-pressure steam is suppressed so that an insertion unit can maintain required properties.

Figure 7:
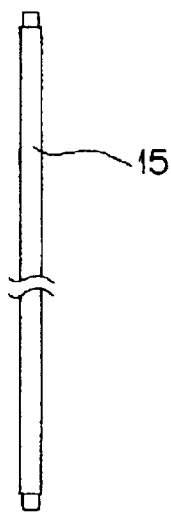
FIG. 7 is an explanatory diagram showing a first method for annealing a flexible tube included in a third embodiment.
Figure 8:
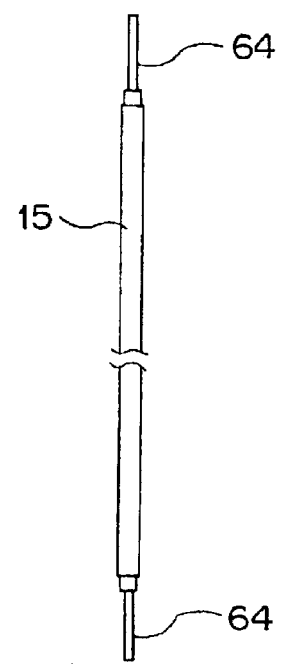
FIG. 8 is an explanatory diagram showing a second method for annealing the flexible tube included in the third embodiment.
Figure 9:
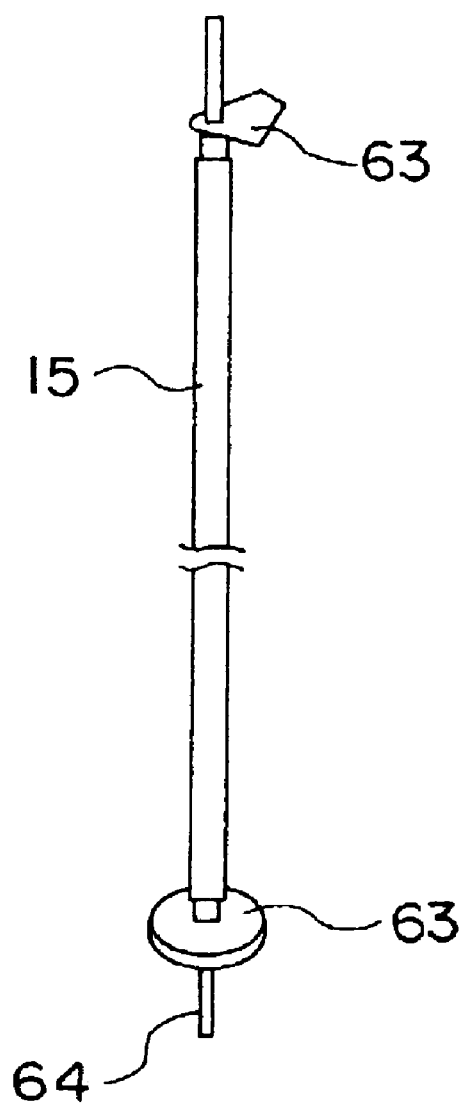
FIG. 9 is an explanatory diagram showing a third method for annealing the flexible tube included in the third embodiment.

FIG. 7 to FIG. 9 are concerned with the third embodiment of the present invention. FIG. 7 is an explanatory diagram showing a first method of annealing a flexible tube. FIG. 8 is an explanatory diagram showing a second method of annealing the flexible tube. FIG. 9 is an explanatory diagram showing a third method of annealing the flexible tube. In the description of the third embodiment, components not shown in FIG. 7 to FIG. 9 will be described with reference to FIG. 1, FIG. 3, and FIG. 4.

(Configuration)

As shown in FIG. 1, FIG. 3, and FIG. 4, the flexible tube 15 of the endoscope 2 has the armor layer 40 layered over the helical tube 38 and braid tube 39 thereof.

The flexible tube 15 is incorporated in the endoscope 2 with both ends thereof secured by bonding the metallic members that are the distal metal fitting 37 and joint metal fitting 41 to the both ends using an adhesive or the like.

The armor layer 40 is made of a material whose softening point is high, for example, an ester elastomer, a styrene resin, a fluoro rubber, or a silicon rubber so that the armor layer 40 can maintain its softness and other properties even when exposed to high-temperature steam. There is a possibility that when these materials are heated to about 150° C. or higher, the resins thereof may be largely denatured. For this reason, before the flexible tube 15 is incorporated in the endoscope 2, the flexible tube is annealed in an atmosphere ranging from about 115° C. to about 150° C. Moreover, the flexible tube is left in the atmosphere for a certain time interval ranging from 30 minutes to 2 hours.

In the third embodiment, therefore, the endoscope 2 has the insertion unit 7 that includes the flexible tube (flexible tube 15) having an armor layer, which is made of a resin, as an external surface thereof. Before the flexible tube 15 is incorporated in the endoscope 2, the flexible tube 15 is annealed in the atmosphere of about 115° C. or higher.

Now, first to third methods of annealing the flexible tube will be described below.

As shown in FIG. 7, according to the first annealing method, the flexible tube 15 is retained straight with no tensile force imposed thereon, and annealed horizontally.

As shown in FIG. 8, according to the second annealing method, the flexible tube 15 is retained vertically with a core 64 passed through it, and then annealed.

In order to retain the flexible tube 15 vertically, the position of the lower end of the flexible tube 15 may be defined and the weight of the flexible tube 15 itself may be utilized.

As shown in FIG. 9, according to the third annealing method, the core 64 is passed through the flexible tube 15, and both ends of the flexible tube 15 are contracted by a defined magnitude using defining members 63. The flexible tube 15 is then annealed.

(Action)

According to the third embodiment, the flexible tube 15 is annealed. Thus, residual stress occurring in the course of manufacture can be removed.

Since the flexible tube 15 is annealed before being incorporated in the endoscope 2, the insertion unit 7 is realized as a member little affected by denaturation which the armor layer 40 of the flexible tube 15 undergoes due to heat dissipated therefrom or residual stress like stretch occurring during molding. Moreover, since the flexible tube 15 is retained straight during annealing, the resin made into the flexible tube will not be denatured. Consequently, the flexible tube will not be prone to bend. Moreover, since the lower end position alone of the flexible tube 15 is defined, the weight of the flexible tube 15 itself is used to impose a load on the flexible tube 15 in a longitudinal direction in which the flexible tube contracts. Consequently, deformation stemming from heat dissipated from the resin itself or residual stress can be nullified to the greatest possible extent. As mentioned above, generally, the condition of a temperature for a sterilization step within a high-pressure steam sterilization method ranges from about 115° C. to about 138° C. Consequently, even when the flexible tube 15 incorporated after annealing is sterilized through high-pressure steam sterilization, occurrence of residual stress or contraction can be suppressed.

Moreover, when the flexible tube 15 is annealed while being contracted by a defined magnitude of deformation, a thermal deformation occurring thereafter can be suppressed to be smaller than a magnitude of thermal deformation which a resin itself made into the flexible tube undergoes. Moreover, because the flexible tube 15 is annealed before having both ends thereof secured with the distal metal fitting 37 and joint metal fitting 41, distortion or deterioration of the portions of the flexible tube secured with the distal metal fitting 37 and joint metal fitting 41 caused by a thermal load stemming from high-pressure steam sterilization can be nullified.

(Advantages)

As described above, according to the third embodiment, the flexible tube having annealed in an atmosphere of about 115° C. or higher is incorporated in the endoscope 2. Therefore, even when the endoscope 2 is sterilized through high-pressure steam sterilization, the insertion unit 7 exhibits desired resistance and softness. Moreover, even if contraction occurs, the magnitude of contraction is limited. The desired properties of the insertion unit can be ensured. Consequently, even when the endoscope 2 is repeatedly sterilized with high-pressure steam, the denaturation of the resin made into the flexible tube can be suppressed. The properties required for the insertion unit can be maintained, and excellent inserting smoothness can be ensured.

In the present invention, it is apparent that a wide range of different modifications can be made on the invention without a departure from the spirit and scope of the invention. The present invention is not restricted to any specific embodiment but is limited to the appended claims.

What is claimed is:

1. An endoscope device comprising:

an insertion unit; and an operation unit coupled to said insertion unit, wherein the operation unit has (i) a casing that constitutes at least a part of an outer surface of the operation unit and
(ii) a built-in component having heat conductivity, and
wherein a drop in temperature when the operation unit is cooled within a predetermined range of temperatures is made substantially equal to or larger than a drop in temperature of at least part of an external surface of the insertion unit by rendering at least part of the casing close to or in contact with the built-in component to promote cooling of the casing.

2. The endoscope device according to claim 1, wherein the operation unit has a grip portion by which an operator grasps the operation unit; and
wherein the casing constitutes an outer surface of the grip portion.

3. The endoscope device according to claim 1, wherein at least part of the casing is made of a material exhibiting better heat conductivity than that of a material of at least part of an external surface of the insertion unit.

4. The endoscope device according to claim 1, wherein said predetermined range of temperatures within which said operation unit and insertion unit are cooled is from substantially 35° C. to substantially 140° C.

5. The endoscope device according to claim 1, further comprising a holder member for holding the casing, the holder member contacting at least part of the external surface of the casing,
wherein heat dissipated from at least part of the external surface of the casing is conveyed to the holder member.

6. The endoscope device according to claim 5, wherein said holder member is made of a material exhibiting better heat conductivity than that of a material of at least part of the external surface of the casing.

7. The endoscope device according to claim 1, wherein the surface of the casing is configured to promote cooling of the casing.

8. An endoscope device comprising:
an insertion unit;
an operation unit coupled to the insertion unit and including a casing that constitutes an outer surface of the operation unit; and
a heat absorbing material provided adjacent to at least part of the casing so as to promote cooling of the casing, the heat absorbing material having a better heat conductivity that that of a material constituting at least part of the casing.

9. The endoscope device according to claim 8, wherein the operation unit is cooled within a predetermined range of about 35° C.–140° C.

10. The endoscope device according to claim 8, further comprising a holder member for holding at least the casing, wherein the holder member holds the casing, the holder member contacts at least part of the external surface of the casing, and heat dissipated from at least part of the external surface of the casing is conveyed to the holder member.

11. The endoscope device according to claim 10, wherein the holder member is made of a material exhibiting better heat conductivity that that of a material of at least part of the external surface of the casing.

12. The endoscope device according to claim 8, wherein the surface of the casing is configured to promote cooling of the casing.

13. An endoscope device comprising:
an insertion unit;
an operation unit which is coupled to said insertion unit and which an operator grasps for handling it, wherein the operation unit has a casing that constitutes an armor of the operation unit, and
wherein the operation unit includes heat radiating means as at least part of the external surface thereof so as to promote the cooling of the casing, and
wherein a drop in temperature of the heat radiating means when the operation unit is cooled within a predetermined range of temperatures is substantially equal to or larger than a drop in temperature of at least part of the external surface of the insertion unit.

14. The endoscope device according to claim 13, wherein said heat radiating means is made of a material exhibiting better heat conductivity than that of a material of at least part of the external surface of said insertion unit.

15. The endoscope device according to claim 14, wherein said heat radiating means is disposed adjacently to another member that is included in said operation unit and that is made of a material exhibiting poorer heat conductivity than that of a material of said heat radiating means.

16. The endoscope device according to claim 13, wherein said heat radiating means includes a grip casing member by which an operator grasps said operation unit.

17. The endoscope device according to claim 16, wherein said grip casing member is made of a resin material exhibiting better heat conductivity than that of a material of at least part of the external surface of said insertion unit.

18. The endoscope device according to claim 17, wherein said grip casing member is disposed adjacently to another member that is included in said operation unit and that is made of a material exhibiting better heat conductivity than that of a resin material of said grip casing member.

19. The endoscope device according to claim 13, wherein said predetermined range of temperatures within which said operation unit and insertion unit are cooled is substantially from 35° C. to 140° C.

20. The endoscope device according to claim 13, further comprising holder means for holding said operation unit, wherein:
since said holder means holds said operation unit, said holder means comes into contact with said heat radiating means, and heat dissipated from said heat radiating means is conveyed to said holder means.

21. The endoscope device according to claim 20, wherein said heat radiating means is made of a material exhibiting better heat conductivity than that of a material made into at least part of the external surface of said insertion unit.

22. The endoscope device according to claim 21, wherein said holder means is made of a material exhibiting better heat conductivity than that of a material made into said heat radiating means.

23. The endoscope device according to claim 22, wherein said holder means is made of a metallic material.

24. The endoscope device according to claim 13, wherein the surface of the casing is configured to promote cooling of the casing.

25. An endoscope device comprising:
an insertion unit; and
an operation unit coupled to the insertion unit; and
a grip portion provided on the operation unit which an operator grasps,
wherein the external surface of said insertion unit is made of a material that exhibits predetermined heat conductivity when the insertion unit is cooled within a predetermined range of temperatures; and
wherein the external surface of the grip portion is made of a material that exhibits substantially the same or better heat conductivity as or than that of the material of at least part of the insertion unit when the operation unit is cooled within the predetermined range of temperatures, thereby promoting cooling of the grip portion.

26. The endoscope device according to claim 25, wherein said grip portion includes a grip casing member that serves as an outline member, and a metallic member that comes into contact with the surface of said grip casing member and that exhibits substantially the same or better heat conductivity as or than that of said grip casing member.

27. The endoscope device according to claim 25, wherein the surface of the casing is configured to promote cooling of the casing.

* * * * *